(12) United States Patent
Peck et al.

(10) Patent No.: US 12,364,394 B2
(45) Date of Patent: Jul. 22, 2025

(54) SYSTEM AND METHOD FOR RADIOPHARMACEUTICAL THERAPY ANALYSIS USING MACHINE LEARNING

(71) Applicant: BAMF Health LLC, Grand Rapids, MI (US)

(72) Inventors: Anderson Peck, Grand Rapids, MI (US); Ting-Tung Chang, Grand Rapids, MI (US); Jeffrey Lee VanOss, Kentwood, MI (US); Stephen Moore, Singapore (SG)

(73) Assignee: BAMF Health LLC, Grand Rapids, MI (US)

( * ) Notice: Subject to any disclaimer, the term of this patent is extended or adjusted under 35 U.S.C. 154(b) by 601 days.

(21) Appl. No.: 17/190,301

(22) Filed: Mar. 2, 2021

(65) Prior Publication Data
US 2022/0142480 A1     May 12, 2022

Related U.S. Application Data

(60) Provisional application No. 63/110,491, filed on Nov. 6, 2020.

(51) Int. Cl.
*G16H 30/40* (2018.01)
*A61B 5/00* (2006.01)
(Continued)

(52) U.S. Cl.
CPC .......... *A61B 5/0036* (2018.08); *A61B 5/0035* (2013.01); *A61B 5/055* (2013.01); *A61B 6/032* (2013.01); *A61B 6/037* (2013.01); *A61B 6/50* (2013.01); *A61N 5/1001* (2013.01); *G06N 20/00* (2019.01); *G06T 7/11* (2017.01); *G06T 7/174* (2017.01); *G16H 20/40* (2018.01); *G16H 30/40* (2018.01); *G06T 2207/10081* (2013.01); *G06T 2207/10088* (2013.01); *G06T 2207/10104* (2013.01); *G06T 2207/10108* (2013.01); *G06T 2207/20081* (2013.01); *G06T 2207/20084* (2013.01); *G06T 2207/30096* (2013.01)

(58) Field of Classification Search
CPC ..... A61B 5/0036; A61B 5/0035; A61B 5/055; A61B 6/032; A61B 6/037; A61B 6/50; A61N 5/1001; A61N 5/1071; A61N 5/103; A61N 2005/1021; G06N 20/00; G06N 3/045; G06N 3/044; G06N 3/08; G06T 7/11; G06T 7/174; G06T 2207/10081; G06T 2207/10088; G06T 2207/10104; G06T 2207/10108; G06T 2207/20081; G06T 2207/20084; G06T 2207/30096; G06T 7/0016; G16H 20/40; G16H 30/40; G16H 15/00; G16H 20/17; G16H 50/20; G16H 50/70
See application file for complete search history.

(56) References Cited

U.S. PATENT DOCUMENTS

| | | | | |
|---|---|---|---|---|
| 2008/0214933 | A1* | 9/2008 | Von Busch | A61B 8/481 600/431 |
| 2019/0333623 | A1* | 10/2019 | Hibbard | A61N 5/1039 |
| 2021/0183070 | A1* | 6/2021 | Laaksonen | A61N 5/1048 |

* cited by examiner

*Primary Examiner* — Shahdeep Mohammed
(74) *Attorney, Agent, or Firm* — Ted Sabety; Sabety +associates, PLLC NYC

(57) ABSTRACT

A system and method of using machine learning to predict the pharmacokinetics of a therapeutic radiopharmaceutical on a subject patient using the biodistribution data of the patient in order to dynamically treat the patient using the radiopharmaceutical.

28 Claims, 13 Drawing Sheets

(51) Int. Cl.
  *A61B 5/055* (2006.01)
  *A61B 6/03* (2006.01)
  *A61B 6/50* (2024.01)
  *A61N 5/10* (2006.01)
  *G06N 20/00* (2019.01)
  *G06T 7/11* (2017.01)
  *G06T 7/174* (2017.01)
  *G16H 20/40* (2018.01)

SYSTEM AND METHOD FOR RADIOPHARMACEUTICAL THERAPY ANALYSIS USING MACHINE LEARNING

PRIORITY CLAIM

This is a utility patent application which claims the benefit of U.S. Provisional Patent Application No. 63/110,491 filed on Nov. 6, 2020 which is hereby incorporated by reference in its entirety for all that it teaches herein.

FIELD OF INVENTION

This relates to image processing and machine learning in a specific way to enable and improve radiopharmaceutical therapy analysis.

BACKGROUND

Radiopharmaceutical therapy involves the targeted delivery of radiation to tumour cells. A Radiopharmaceutical is a drug that can be used either for diagnostic or therapeutic purposes. In one embodiment, it is composed of a radioisotope of an element bonded within an organic molecule. Other embodiments may be non-organic molecules. The bound molecule conveys the radioisotope to specific organs, tissues or cells. The radioisotope is selected for its properties and its treatment utility. This treatment approach is distinguished from external beam radiotherapy and brachytherapy (radioactive seed placement) in that the radiation is delivered by unencapsulated radionuclides through an injectable solution or suspension that is distributed throughout the body, rather than localized to the site of injection. Similarly, radioactive seeds are also localized once they have been placed in the body. In contrast, the Radiopharmaceutical is systemic Radiopharmaceutical dosimetry describes the interaction between the energy deposition associated with a radiopharmaceutical's emissions and the patient's body and helps to guide optimal clinical use of radiopharmaceuticals. Dosimetry reports used in today's medical field are to quantify administered amounts of radioactivity to the absorbed radiation dose in tumours, organs, or the whole body. Dosimetry is important for dose correlation with clinical results, and in some instances, for treatment planning to avoid excess toxicity. Currently the preparation of a dosimetry report is a manual effort by a radiologist which is time a consuming process. Current conventional imaging (CT, MRI, bone scan) are mostly unable to localize disease recurrence (when tumours are small) for example in Prostate cancer if PSA levels are low. Prostate PET ligands fill this diagnostic void of hidden disease and allow a chance at early detection.

A radiopharmaceutical or radioactive drug is a form of a compound in a solution where the atomic structure is using an isotope that is detectable via different scanning machines. The radioactive drugs are administered in a non-invasive way through an injectable solution or suspension. Each radioactive drug will target and bind to a different molecule. For example in a case of treating prostate cancer, the radioactive drug (Lutetium 177) would bind to the PSMA ligand which is bound to the radioisotope. Radiologists calculate the dosimetry calculations by analysing the CT, PET and SPECT scans using software as an aid to manually segment the region of interest (ROI) including filtering organs and background organs and tumors. Filtering organs and background organs are ones where some partial uptake of the radioactive drug (absorption of radiation is observed) on the imaging output. See FIG. 4 for an example of the highlighted (level of uptake) areas in a PET scan due to a radioactive drug being administered. The uptake values correlate to the amount of absorbance of the radioactive drug and thereby the amount of energy absorbed is recorded for organs and tumors and is presented to form the dosimetry report. This report is what is used by physicians to determine the treatment and to monitor the therapy.

SUMMARY

In one embodiment of the invention, the system and process generates a predicted SPECT scan of a patient out of an earlier PET scan and an earlier CT scan of a patient combined with the selection of the type and amount of radiopharmaceutical administered to the patient. By using a machine learning process, the system can predict the pharmacokinetics of the radiopharmaceutical administered during the therapeutic phase using the PET scan and CT scan acquired during the diagnostic phase. In addition, the system and method can adjust its prediction as actual SPECT scans are conducted during the therapeutic phase in order that the next series of SPECT prediction be improved in accuracy and the prescribed therapy thereby adjusted. In yet another embodiment, generating predicted SPECT scans over future time intervals can result in a prediction of the efficacy of the prescribed radiopharmaceutical, its dosage and timing, and whether the prescribed radiopharmaceutical is the best choice for a given patient.

In an embodiment, there is a method to automatically generate nuclear medicine/dosimetry reports using machine learning algorithms for efficient use in clinic diagnosis and treatment. Synthetic dosimetric scans may be generated from diagnostic PET scans, patient data and the prescription of radiopharmaceutical to be administered to the patient.

In an embodiment, there is a method for accurately predicting an optimal therapy dose.

In an embodiment, there is a method for tumour tracking and tumour analysis across multiple scans, and an automated way to track tumours over multiple scans of the same patent to monitor and measure the relative change of nature of the tumours and the use the relationship between such change and patient characteristics to determine adjustments to the dosage.

In an embodiment a method to use machine learning to predict the results of individualized therapy for nuclear medicine.

DESCRIPTION OF THE FIGURES

The headings provided herein are for convenience only and do not necessarily affect the scope or meaning of the claimed invention. In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced (e.g., element 101 is first introduced and discussed with respect to FIG. 1).

DETAILED DESCRIPTION

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other features not described in detail herein. Additionally, some well-known structures or functions may not be shown or described in detail below, so as to avoid unnecessarily obscuring the relevant description. The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

Figure 5:
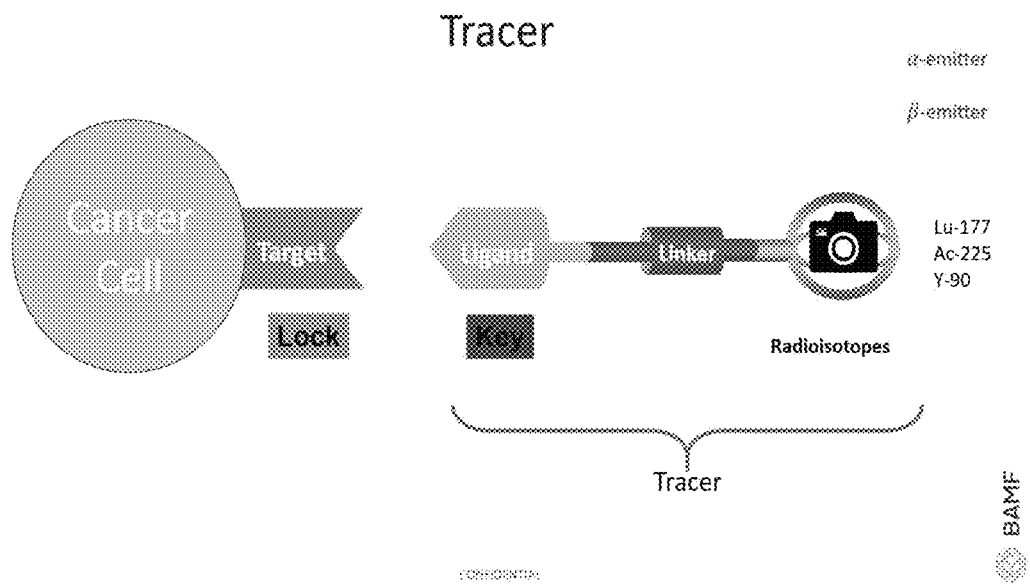
FIG. 5: An example of a radioactive drug as a diagnostic compound for Prostate cancer treatment FIG. 6. An example of a radioactive drug as a therapeutic radioactive compound.
Figure 6:
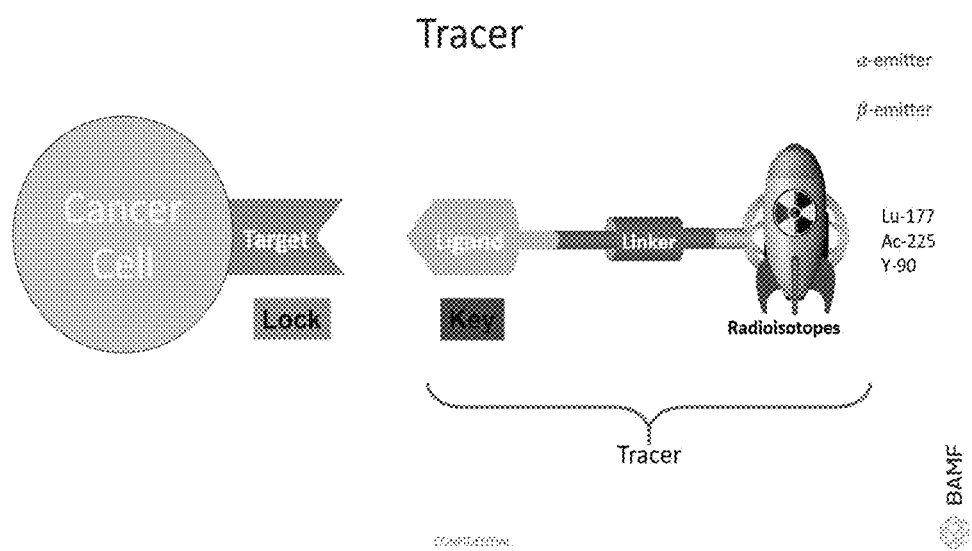

The theragnosis's process has two interacting sub-processes: diagnostics and therapy. Both sub-processes use radioactive drugs but for two different purposes. A first radioactive drug may be selected and administered in order to conduct diagnosis and a second drug selected and administered for therapy. Both processes involve imaging by detecting radiation. In the first step, the radioactive drugs are administered to the patent as part of the diagnostics process and this will highlight the uptake of that particular drug on the PET and SPECT scans. FIGS. 5 and 6 outlines how the radioisotopes are delivered to the cancer cells in the diagnostic and therapeutic phases. The main difference in the diagnostic radioactive compound and the therapeutic radioactive compound is the different elements used for the radioisotopes that bind to the same ligand. In one embodiment related to treating prostate cancer, PSMA ligands are the delivery mechanism. PSMA is a surface transmembrane glycoprotein, present in the epithelium of prostatic ducts. It is highly overexpressed in prostate cancer. Gallium 68 can be used as the radioisotope for diagnostics in this embodiment and since it's a position emitter, a PET scan can be used to highlight the areas where the uptake of the Gallium 68 can be detected. In this embodiment the therapeutic radioactive drug can be comprised of Lutetium 177 or Actinium 225, beta and alpha emitters respectively. In one embodiment a SPECT scanner can read the scan after the therapeutic is administered to highlight the areas where the cancer tumors are present. In other embodiments, different diagnostics and therapeutic compounds can have different emitting radioisotopes that will require different types of scanners to read the effect of the compounds. For example when a radioactive compound for diagnosis is used in prostate cancer like Gallium 68 as it gives off positrons a PET scanner can detect the radiation. However with Lutetium 177 or Actinium 225 (these are beta or alpha emitters) a SPECT scanner may be used to read the radiation delivery result by correlating the detected gamma radiation given off by the isotopes.

The claimed invention utilizes a machine learning engine to analyze the patient's scanned images in order to generate output data representing organ and tumor segmentation, tumor tracking and analysis and dosimetry calculations. The machine learning engine may be comprised of a neural network, preferably a correlated neural network that is specifically trained using image data from a population of patients and a set of correct organ and tumor segmentations. The system and method automates the generation of a therapeutic dosage recommendation and a predicted result scan, which is indicative of the effectiveness of the therapy. In one embodiment, the result scan is a SPECT scan.

Machine Learning Engine (MLE)

The machine-learning engine is comprised of sub-modules that can be referred to as "neurons", although this doesn't literally refer to a biological neuron. The machine-learning neuron is typically an instance of a computer code module that exhibits characteristics like a neuron. For example, the output of a neuron can be a binary 1 or 0, determined whether the linear combination of the inputs to the neuron are equal to or greater than a threshold. In one embodiment, a neuron is represented by a set of computer code that when executed by the computer, causes it to calculate the linear combination of the neuron inputs, apply a thresholding function and then store an output value. Each neuron may be represented in one or more data structures as a set of input data, a set of coefficients and an output data value. The neuron program code itself may be called as a program sub-routine that is applied to each neuron data structure. The basic neuron calculation may be represented by this formula:

$$N=1 \text{ if } (\Sigma \text{Input}_i \cdot \text{Coeff}_i > T) \text{ or } 0 \text{ otherwise}$$

Where the i represents the ith input into the neuron. The index i ranges from zero to I, where I is the number of inputs into the neuron. In its most general form the function applied to the dot product is referred to as the activation function, which may take many forms. In some embodiments, the conditional in the expression may be replaced with a max function, such that the activation function is:

$$N=\max(\Sigma \text{Input}_i \cdot \text{Coeff}_i, 0)$$

Each neuron can be indexed, such that for a single layer array of J neurons, each represented by $N_j$ with j between 0 and J and each getting I inputs:

$$N_j = 1 \text{ if } \left(\sum_{i=0}^{I} \text{Input}_i \cdot \text{Coeff}_i > T\right) \text{ or } 0 \text{ otherwise.}$$

There can be layers of neurons, where the lowest layer of neurons get $\text{Input}_i$ but the higher layers get as input the output of the prior neuron layer. The higher jth layer may be represented by:

$$N_{i,j} = 1 \text{ if } \left(\sum_{i=0}^{I} N_{i,j-1} \cdot Coeff_{i,j} > T\right) \text{ or } 0 \text{ otherwise.}$$

The value I, where i=(0<i<I) represents the number of neurons per layer and J, where j=(0<j<J) is the number of layers.

Note that while this formalism appears to have each neuron of layer j−1 feeding its output to each next neuron layer j, if the $Coeff_{i,j}$ for that connection equals zero, it is as if there was no connection at all. In a preferred embodiment, the machine-learning components are comprised of one or more transformer models. The input of an image into the lowest layer of neurons may be accomplished under this formalism by mapping each pixel to a lowest level $Input_i$. This may be by having each row of pixels in the image map to a different set of inputs in the lowest layer. For example, consider a 1028×1028 pixel image (low resolution, but as an example), the $1029^{th}$ input can represent the first pixel of the second row of the image. That is, for any pixel presented to $Input_i$, the $Input_{i+1028}$ is the pixel one row above the pixel presented to $Input_i$. To the extent the next level of neurons take as input lower level neurons corresponding to neighboring pixels in 2 dimensions, the values of the $Coeff_{i,j}$ will reflect the topology. For example $Coeff_{i,j}$ and $Coeff_{i,j+1028}$ would represent two weights at layer i for two pixels in the same column but neighboring rows in the image.

For a black or greyscale image comprised of pixels, the inputs may be a single integer value. In one embodiment, the range would be 0-255. For a color image, the pixel may be represented by three values together, each representing a corresponding component color (R, G, B), or using other color modelling techniques, like Hue, Saturation and Intensity. In this embodiment, a 2 dimensional image may be input into the lowest layer of a machine learning array of neuron modules. An image may be a 2 dimensional array of pixels or a 3 dimensional array of voxel values. When predicting a dosimetry, in one embodiment, the output is a 3D image of voxels, where the voxel values are in becquerel units of radiation activity. Where the output of the MLE is an image or an image with additional data, one embodiment would output a vector of elements, a subset of elements representing a corresponding set of individual pixels or voxels in the predicted image. Similarly, where the MLE is predicting radiopharmaceutical types or predicting administration amounts or times, the vector would include elements assigned to the type output, the time output and the amount output. In order to do this, the training data set has to present the ground truth data, or labelled data as a vector of elements assigned in the same way. Essentially, the image is mapped to a vector input, and a vector input mapped to an image output. To the extent the input to the MLE is an image and other data, the other data is also mapped to a vector, and the image vector and input data vector may be concatenated into one large vector that is submitted into the MLE. Likewise, the reverse may be accomplished with the vector on the output of the MLE.

The network of neurons, when trained for a task, has a set of coefficients $Coeff_{i,j}$ that configure the array. In order to determine these coefficients, the network is trained. Training is accomplished by presenting a set of PET scans, CT scans, SPECT scans and the matching patient data to the network, and comparing the predicted SPECT image to an actual SPECT image of the same patient. An additional input can be the scan time values associated with the PET and SPECT images in the training set, representing a date and time when the scans were taken. In addition, the the date and time of administration of the therapeutic radiopharmaceutical can be extracted from the EMR data set and input into the machine learning module. The differences between the predicted SPECT image for given future time value and the actual SPECT image at that time is an error image. With the objective of obtaining an error image of zeroes in all locations in the image, a training algorithm may be applied that adjusts the coefficients $Coeff_{i,j}$ so that the next iteration produces a smaller or lower value error. This process is repeated until the system has reached an error that is at or below a predetermined sufficient error threshold. In one embodiment, the error image may be converted to a single error parameter that is used as input to calculate the over all quality of the result and to make adjustments to the coefficients. In another embodiment, the difference between each output vector representing the output image and attendant parameters to the input vector representing the input image and attendant parameters, can be expressed as an error vector $E_i$ where each of the i elements is used to adjust the coefficients of the neurons upon which output vector element i is dependent. The objective is to have $E_i$ to have all zeroes as elements.

In another embodiment, the relative error quality of vector E can be calculated as a Euclidian vector length of E: the longer the vector, the more error in the result. In this embodiment, the training process is repeated until the length of error vector E is less or equal to a predetermined parameter value representing the quality of the prediction. For multiple training predictions, where the entire training set is applied to the MLE, there will be a set of error vectors $E_{i,j}$ with i representing the ith element in the output vector and j the jth member of the training data set (that is, a pair of known input and output data, also referred to as a ground truth). In this case, the objective is to adjust the coefficients in order that a predictive quality is achieved across the entire set of actual data. This may represented as all of the $E_{i,j}$ vectors being below some threshold length. Alternatively, it could be calculated as the vectors occupying a volume in j space (j dimensions) that is less than a predetermined data value representing the quality of the training.

Full training can include the EHR data and scans for a large number of patients. This data will also include the type of radiopharmaceutical administered at what amount and which time intervals. The types of pharmaceuticals can be represented by a numeric index number in order that the MLE can use it as input into the process. In this embodiment, the output data can include a radiopharmaceutical index number, which would mean the trained MLE can predict which radiopharmaceutical is predicted to produce the best result. In addition, the output data can include time values and dosage amounts. This would result in an MLE that can predict the type of drug, its amount and timing of administration as the predicted optimal result based on the patient's PET scan and the patient history.

Figure 7:
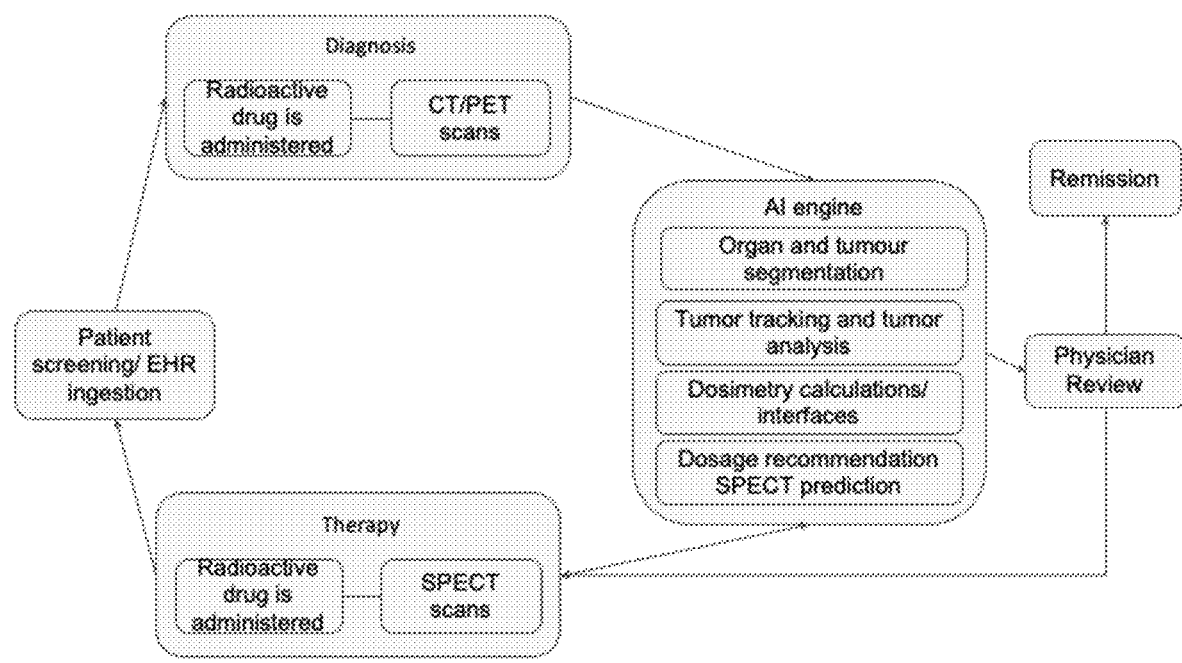
FIG. 7. One embodiment of the invention using a machine learning engine to analyse tumour profiles FIG. 8. Typical CNN architecture as the machine learning engine FIG. 9. Organ Segmentation diagram using machine learning.

FIG. 7 shows one embodiment of a system architecture with the MLE integrated with the modules of the radiopharmaceutical therapy process. In one embodiment, each module is represented by its own set of coefficients: that is, the same machine learning process may use four different coefficient sets in order to obtain the function of four modules. The MLE is made of up 4 main modules:

Organ and tumour Segmentation module.
Tumour tracking and analysis module.
Dosimetry and Clinical report generation module.
Dosage recommendation and predicted SPECT scan generation module.

Organ and Tumour Segmentation

Figure 1:
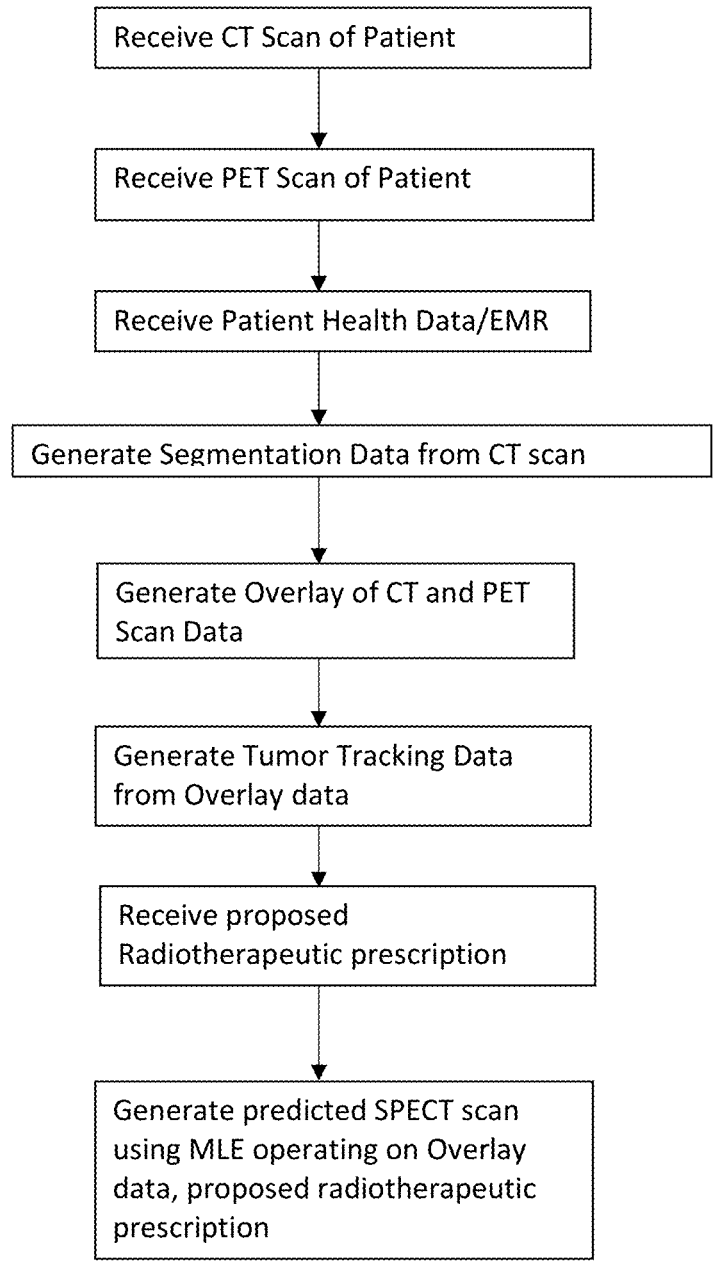
FIG. 1 Flowchart depicting one embodiment of the claimed invention
Figure 2:
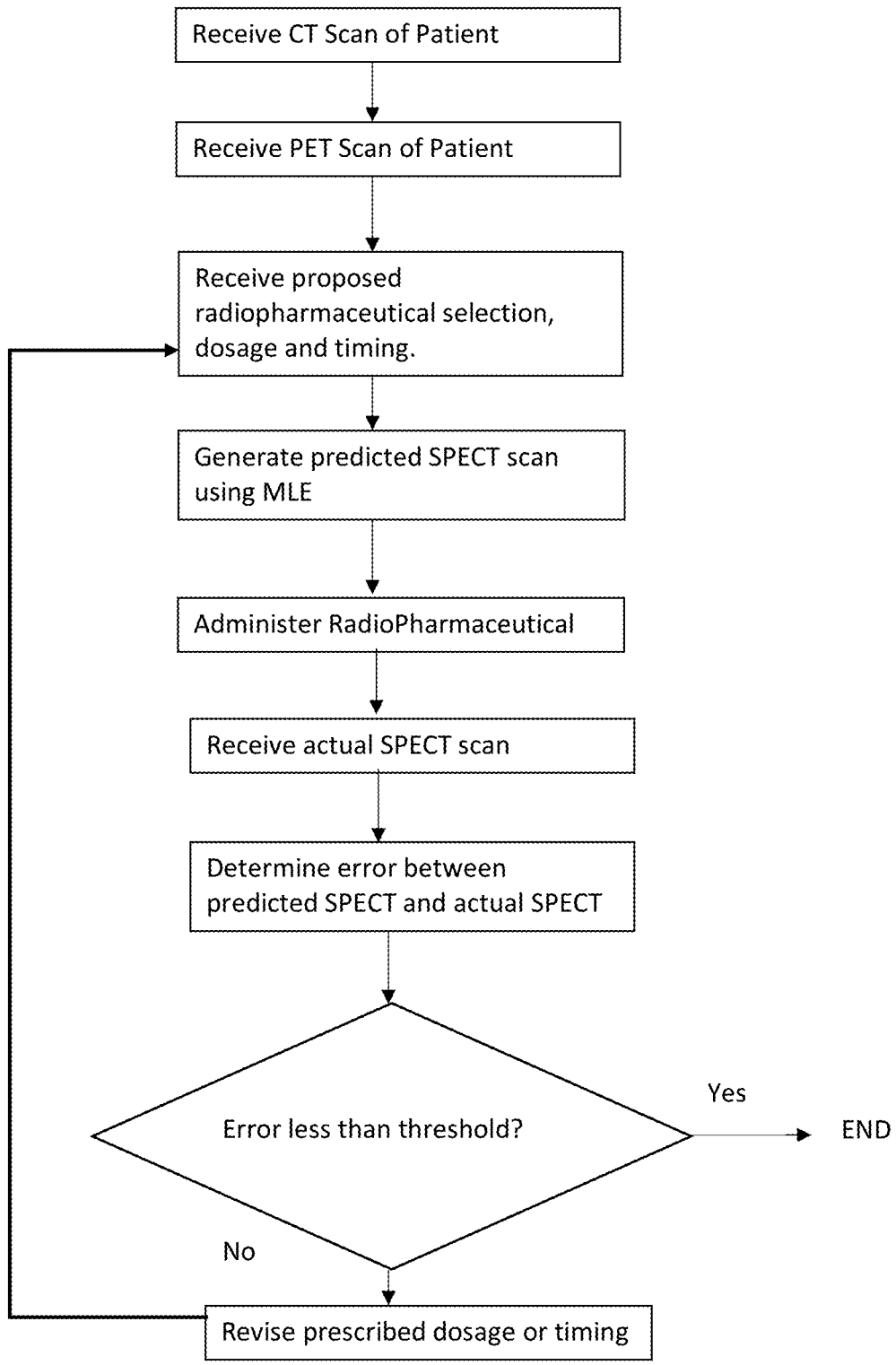
FIG. 2 Flowchart depicting a second embodiment of the claimed invention
Figure 3:
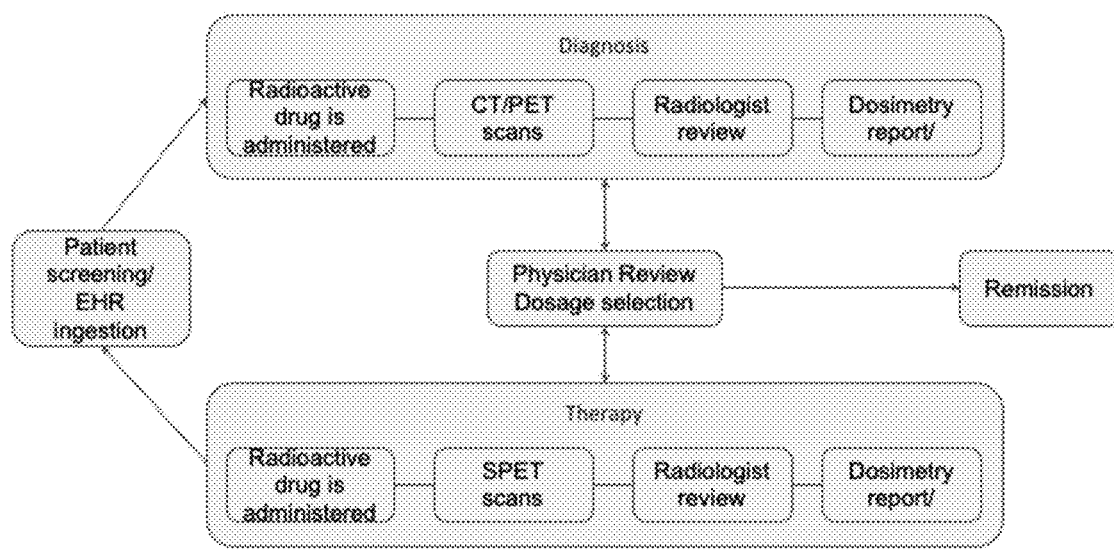
FIG. 3 Overview of current process to treat a patient using Radiopharmaceutical drugs FIG. 4 CT scan on the left, PET scan in the middle and the two scans registered & overlaid on the right
Figure 4:
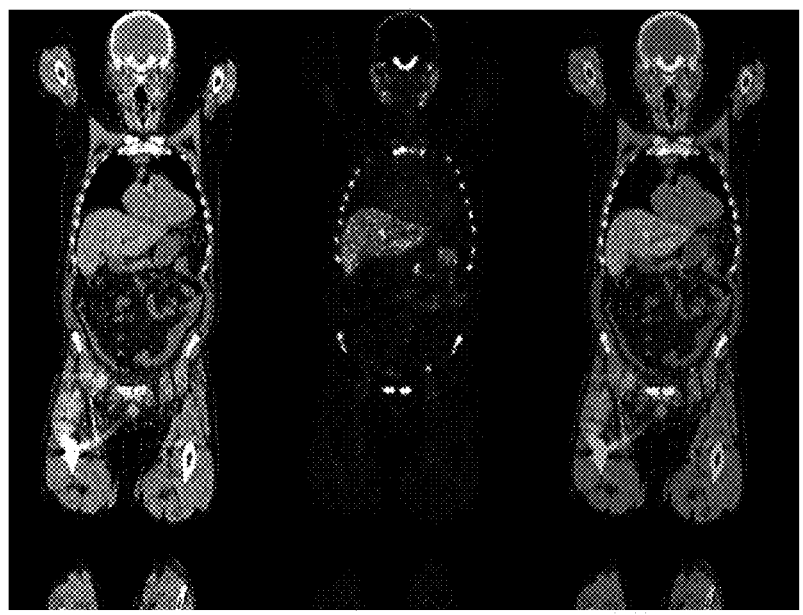

During the diagnosis and the therapy process the radioactive compound that is administered will be inspected by imaging scans. For this explanation we will focus on PET and CT scans as examples. However, different image scanner machines will be used depending on the radioactive drug. A CT scan shows the anatomical structure of the body as a map of the internal densities (FIG. 4 left side). Edges between structures of differing densities, such as organs and skeleton, can be identified in a CT scan. The PET scan shows the uptake location of the diagnostic radiopharmaceutical. While the diagnostic radiopharmaceutical is in the blood, it circulates around the body and it either binds to a target in the tumor, or it is filtered out of the body. In one embodiment where the radioactive compound is for the PSMA treatment, the blood will be cleaned by filtering organs and this will lead to the uptake for example in the liver, kidneys, spleen, and bladder. In this embodiment each of these filtering organs will need to be segmented so they can be distinguished from tumours in the PET scan and also to understand the level of filtering organ uptake for clinical analysis. Note for different embodiments that use other radioactive compounds, which of the organs will show uptake unrelated to the tumor may vary. However, the segmentation of the patient image is still conducted. Other non diseased regions in the body may express the same targeting molecule corresponding to the diagnostic radiopharmaceutical, and so the diagnostic radiopharmaceutical will bind to them. These regions are referred to as off target uptake. In this embodiment the salivary glands have PSMA expressing cells and thus will show uptake on the PET scans. Once all the relevant organs (filtering and off target) for a particular radioactive compound are segmented on the CT scan, the CT and the PET scans can be registered and the CT segmentations overlaid on the PET scan. Registration may be accomplished by automatically scaling the geometry of the two images in order that features that correspond to each other occupy the same locations in the resulting output overlay image. In one embodiment, a first data structure representing the pixels and their location in the PET image may be altered using matrix multiply techniques to change the assigned pixel locations to match certain features with a second data structure representing the pixels of the CT image. FIG. 4 shows on the right hand side the overlay of the two scans.

Figure 8:
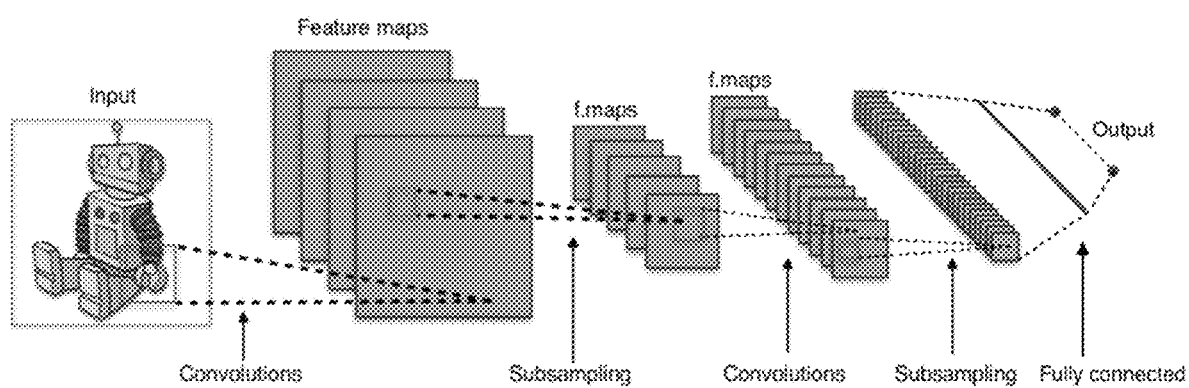

The MLE is used to accomplish the segmentation in order that it be automated. Identifying the pixels/voxels in the images corresponding to certain organs or lesions from background medical images such as CT or MRI images by using machine learning is a way to speed up this process for medical clinics. Many algorithms from edge detection filters, and mathematical methods extracting hand-crafted features can be applied to this problem. Deep learning models are also well suited to the problem. In particular, Convolutional Neural Networks (CNNs) are well suited to this type of problem and give accurate results. A CNN is a branch of neural networks and consists of a stack of layers each performing a specific operation, e.g., convolution, pooling, loss calculation, etc. Each intermediate layer receives the output of the previous layer as its input, as depicted in FIG. 8. The beginning layer is an input layer, which is directly connected to an input image with the number of neurons equal to the number of pixels in the input image. The article ImageNet Classification with Deep Convolution Neural Networks, Krizhevsky, Sutskever, Hinton, Communications of the ACM, June 2017, Vol. 60, No. 6, pg. 84, is incorporated by reference.

But this embodiment is not limited to CNN's, other type of deep learning network architecture may be used, such as, not limited to:

Convolutional Residual Networks (CRNs)

Recurrent Neural Networks (RNNs)

Contextual LSTM

In these arrangements of MLE architecture, the output of a given neuron in the network may be a function of both the neuron outputs of the layer below, but also combined with a set of outputs from a layer ahead. In a convolution architecture, the output of a given neuron may be a combination of the outputs of neurons on the next layer down, but selected such that the neurons represents a portion of the image surrounding a point in the image. In addition, at each layer i, there may be applied a set of coefficients or parameters representing a kernel of a convolution calculation that generates an calculation output for the next layer i+1. The kernel may be designed to detect a particular feature, or a data layer whose contents are the detection of the designated feature the kernel may filter for. The MLE may be comprised of multiple kernels. In the training process, the coefficients for the kernels may be adjusted to meet the error threshold requirement of the system.

Figure 9:
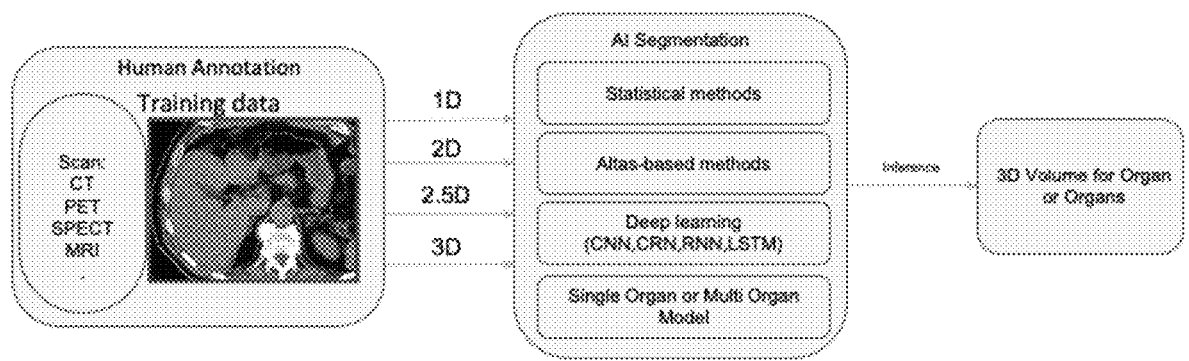

FIG. 9, outlines how from human annotated training data, where organs of interest are manually labelled into 2D slices or 3D volumes, is used to train the MLE. The slices or volumes are used as input to the MLE. The annotation labels are then considered the ground truth for MLE. They are used to train a deep learning based system described in this section. The output of the MLE is compared to the corresponding human annotation in order to measure an error. That error is used to adjust the coefficients or weights comprising the MLE. This iterative process is conducted until the error across the data set is less than a predetermined threshold.

Figure 10:
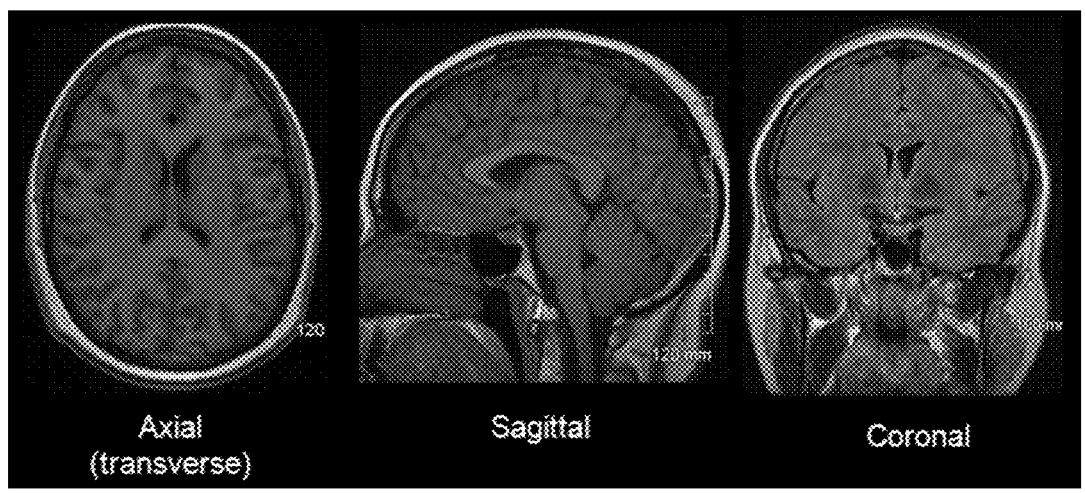
FIG. 10. Planes used to extract 2D images from CT scans

Several different methods can be used to feed the data from a 3D volume into the network to learn the labelled regions. In one embodiment a 2D input into a CNN can be applied. 2D images taken from scans are passed to the input layer of a CNN in various image channels. These 2D images are usually taken from the views outlined in FIG. 10 (Axial, Sagittal and Coronal).

A 2.5D CNN model is a series of 2D CNN models, each model trained on 2D images from different orthogonal slices of the input volume in additional to the 2D inputs from the standard 2D models, the results of these models are combined into a final output volume. A 3D CNN uses true 3D filters, to maintain volumetric spatial information. 3D CNNs by their nature have more learnable parameters than 2D or 2.5D CNNs, this combined with the large input size of the full volume has historically required large computing requirements that have only recently been realized. Occasionally, tumours may be present in a filtering or off-target organ. In these cases an additional image processing can check the segmented organ region for uniformity or other features in order to identify any suspected tumours. Simple image processing algorithms can be applied to 2D or 3D slices of the scan, like clustering techniques to search for abnormalities that would indicate a tumour with in the organ.

In this embodiment, the order of the segmentation of the organs is irrelevant. The inference model that is the result of the MLE segmentation can be for one organ or for many, depending on the architecture of the system. Multi-organ segmentation aims to segment more than one organ simultaneously. Nonetheless, the objective is segmentation of all the relevant organs and off-target tissue. Once organ segmentation is completed and the CT and PET are overlayed unsupervised machine learning approaches can be used directly on the combined CT/PET scan data to extract all the regions that show radiopharmaceutical uptake that are not in the segmented organs of interest regions. Unsupervised methods can be applied directly on 3D or on 2D data. For example a 2D approach using cluster techniques such as K-means can be applied to find the cluster corresponding to the tumour pixels in an image and the rest of considered non tumour. Prefilter techniques will add like principal component analysis (PCA) to remove noise and enhance results. Alternative methods amongst others to clustering would be connected component analysis (CCA) to identify the regions in a 3D volume that have significant uptake and are candidates for tumours. After the above, the output will be a labelled volume showing regions of potential tumours in the PET scans. These are then filtered by the registered off-target and filtering organ segmentation from the CT scans. PET labelled regions outside of the off-target/filtering organ CT labels are tumours.

In one embodiment there is a data structure for segments:

Segment i: <x, y, z>, bounding box <delta x, delta y, delta z>, type, off-target/filter, scan type The organ type can inserted and an off-target Boolean value. In this simple example, the organ is the shape of a rhombic solid located at x, y and z, with dimensions of delta x, delta y, delta z. However, more detailed geometric definitions may be used. The scan type is filled with either PET or CT. Each of the PET and CT scans are input into a computer system that runs a program to generate the set of segment vectors. An algorithm can then march through N segments from i=0 to N, to see if the bounding box of the segment is for a CT scan bounding box, and if there are any PET bounding boxes that overlaps entirely. If not, then that part of the PET bounding box that does not overlap the CT bounding box is converted into a tumor feature vector, at the location calculated using the geometric information to be non-overlapping. The detected region can be considered a region of interest or ROI.

In another embodiment an AI inference engine can be trained directly to identify the tumours without the intermediate step of segmenting organs of interest. This can be achieved if sufficient data is labelled to identify the tumours and the output of the model will be the segments tumours. In this embodiment sufficient training data can be labelled with correct identification and localities of tumors to provide ground truth to train a model to predict and segment PET tumours using a similar method to FIG. 9. The only significant difference being the labelled data input to the AI is now 3D volumes of a PET scan not a CT scan and the 3D volumes will be the tumours not organs.

In yet another embodiment logic based rules can be used to filter 3D volumes directly on the PET scans into tumour or non tumour (filtering organs) classes. These rules could be based in location in the body relative to organs, skeleton structure and size shape characteristics.

Tumour Tracking and Analysis

Once each tumour has been identified on a scan, certain characteristics such as geometry (shape, size, position) and uptake value are recorded. Each tumour can be identified based on these characteristics and will have a unique identifier code, like a universally unique identifier.

In one embodiment, the system generates output data that populates a data structure for each tumor: Show an example data structure and its elements:

TumorID<Tumor location vector x, y, z>,<Tumor bounding box delta x, delta y, delta z>,<Tumor density value>,<TumerID Pointer>.

(UUID) for tracking this tumour and identification in a database system. If the patient has multiple scans we can tracking the tumours across each of these different scans. The change of tumor size at each time point can be recorded. The data structure includes as an element a pointer to the TumorID of the previous scan. For example the system can execute a process to calculate changes between scans:

Top: Fetch Tumor i
Fetch Tumor i->previous scan
Calculate volume of Tumor i.bounding box
Calculate volume of Tumor i->previous scan.bounding box.
Subtract the two volumes
Store in Delta.x.y.z.
Increment i
Last i?
No: go to top.
Yes: Generate Image using Delta x y z.

This allows us to correlate the treatment variables in one embodiment, dosage of the radioactive compound, in another time between treatments of the radioactive compound for the therapy to the changes of the characteristics of each tumour. In another embodiment, the system can learn to predict the potential change in tumour based on the prescribed therapy or in other patient variables like age, weight, sex, ethnicity, occupation.

Figure 11:
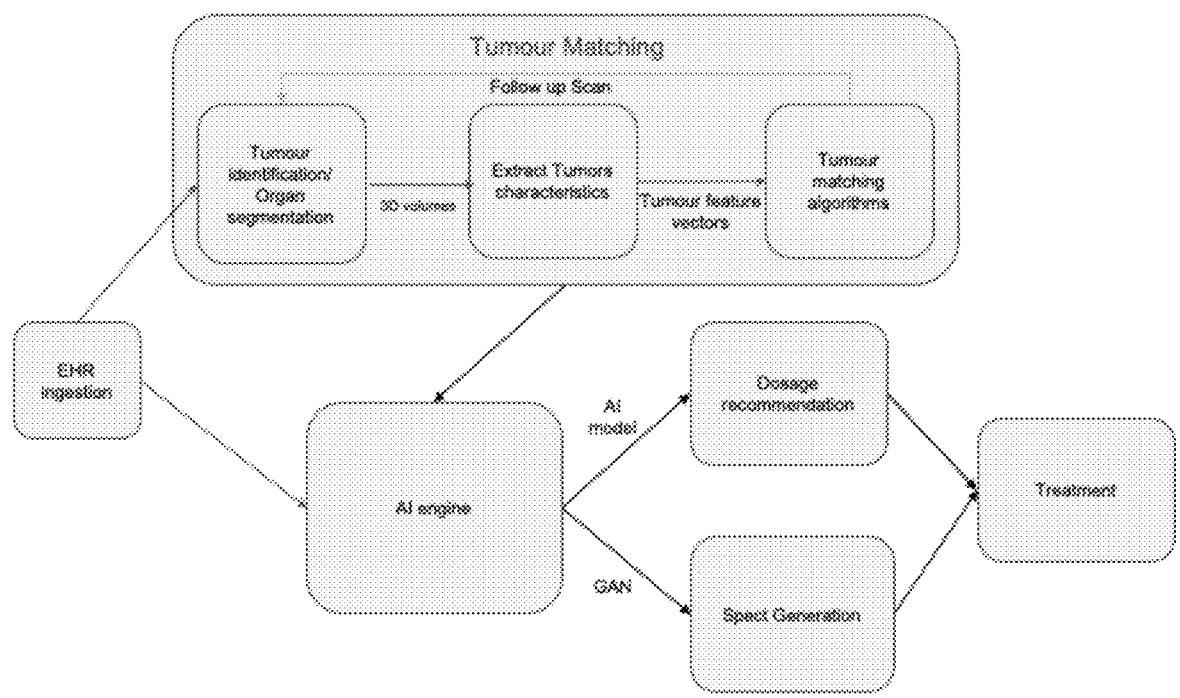
FIG. 11: Tumour Matching and Spect generation overview

For example machine learning can predict how long and how many treatments the patient should get based on the inference from previous patients of the same age and tumour profile. These comparisons can be automatically generated for the dosimetry reports for any and all tumours profiles along with patients data. FIG. 11 is a diagram of this process. The first step is the tumor identification and segmentation process. In one embodiment, this generates a 3D volume data structure with locations of organs, non target areas and tumors. The second step is the extraction of tumor characteristics. This result populates the tumor data structure with feature vectors for each tumor. After the tumour characteristics have been extracted and the feature vector data structure populated, the current scan is matched against the prior scans in order that each tumor feature vector is assigned its corresponding instance in the prior scan. In one embodiment each tumours characteristics will form a feature vector, for example x, y, z position from centre of the scan or some other normalised position in the scan, along with the shape profile of the tumour or a bounding box. Then a weight can be assigned to each of these variables and a distance metric can be applied to search against all the tumours from the comparative scan either exhaustively or with some rules to limit the search. In one embodiment, a distance metric like Euclidean or similar distance metric calculation to find the minimum Euclidean distance and thus the best match for the tumour to be matched. This is effectively a nearest neighbour search to match the tumours to its correspond tumour in the query scan. In another embodiment the matching can be considered a classification problem and use for example an SVM to match feature tumours in a supervised manner where the input would be the feature vector of the tumour profiles into the classifier. The end result is that the data structure with the tumor feature vectors correlates the tumors in scan t with the tumors detected at scan at t−1. In cases where the tumor appears to be new, the null value can be inserted into the data structure as the pointer.

Figure 12:
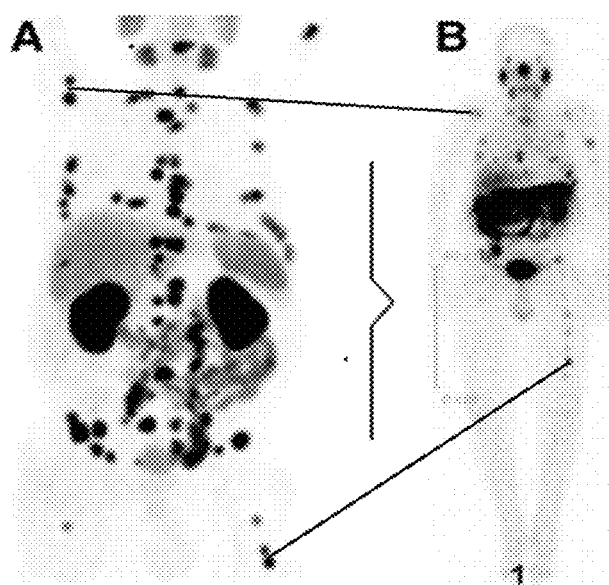
FIG. 12. Tracking Tumours across different types of scans

The above approach to matching tumours can be done for the same scan type of for scans with difference resolutions and different radioactive compounds. As an example. In FIG. 12, A is a PET scan and B is a SPECT scan. The resolution of the PET scan is far superior to the SPECT scan but the tumour profiles of the scans are highly corrected. All of the approaches outlined above can be applied to this type of process as long as the feature vectors are normalised for the different between the scans resolutions. For example the distance x,y,z can be normalised to scale on all input vector rather than an absolute value that would vary across different scan resolutions. The same would applied for the shape and size characteristics to be normalised.

Figure 13:
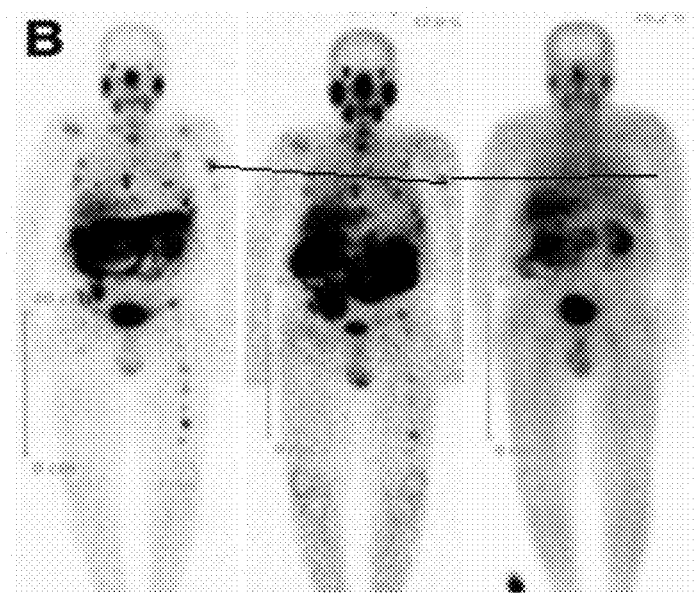
FIG. 13. Tracking tumours across time to analyze changes.

Another embodiment utilizes a configuration where the MLE learns to track tumours in a patient in the same scan type across multiple scans at different time intervals. This is a useful tool to understand the relationship between a treatment and its effect on a patient's tumours as can be seen in FIG. 13. The correlation between the tumours can be modelled over a range of variables like patent characteristics like age, ethnicities and other medical fields to find predicative correlations/causations that can improve/alter a clinic recommendation for treatment based on machine learning models. In one embodiment, creating a regression model linked to exact yearly age and tumour results based on treatment can predict the number of treatments and other analytics that can be applied to patent's. Statistical significance tests must be applied to each model to validate.

The defining goal is to maximize radioactive dose delivered to selected region of interest while minimize dose going elsewhere. In one embodiment, the overall process steps are comprised of:

Receive a PET scan data
Receive identity data of diagnostic radiopharmaceutical.
Receive patient characteristic data (weight, age, sex, etc.)
Receive the identity data of the proposed therapeutic radiopharmaceutical and dosage amounts and timing,
Receive a prediction time value data.
Receive targeted region of interest location data (or may be entire image, or set of selections)
Receive maximum permissible radiodosage threshold data if any for different regions.
Input into machine learning engine;
Generate using MLE a predicted SPECT scan image data for the time value. or a series of predicted SPECT images (or automatically generate N images for N predetermined time values).

In another embodiment, the MLE is trained using as additional input labelled locations of regions of interest in a PET scan. In this way, the MLE is able to automatically determine an ROI for a new PET scan. In yet another embodiment, where the training data set includes the identity of more than one radiopharmaceutical and the corresponding dosage amounts. The resulting MLE can generate predicted SPECT scans for all types of radiopharmaceutical it was trained with and for different amounts of the administered drug. In one variation, the MLE can be run for five drugs, each at 10 different doses. The result would be 50 different predicted SPECT images. The best SPECT result then determines the appropriate drug type and dosage.

Automatic Dosimetry and Clinical Reports

During the current process for radio pharmacies as described in the overview, 2 types of reports are generated which aid in the clinical process. The radiologist report is based on the PET/CT scans and usually for Diagnostics purposes. The second type of report of a dosimetry report which is a report of the actual radiation uptake of the therapy compound. Using the AI engine described in this document with the steps for organ segmentation, tumour identification and tumour characteristics acquisition is the input for these type of reports. Combining this information in an automated way replaces the need to the current approach which is cumbersome and not efficient. Furthermore it allows much more granular detail to track all tumours even if the number of tumours is very high. It allows whole body global statistics to be calculated simply and at far great speeds then current approaches. Currently Dosimetry reports are only generated on request for some patients but with this automated approach this information can be used for all patients due to the effective method of generating it with this approach described in this document.

Dosage Recommendation and SPECT Prediction

SPECT scans are necessary to measure the actual uptake of the therapeutic radiopharmaceutical in the tumors as well as off target, including in filtering organs. This process is time consuming and expensive as many scans are needed to understand the calculation of dosage over time. However, SPECT scans are highly correlated to the diagnostics scans using the CT/PET scans combination This correlation can be learned by using machine learning. In one embodiment, a Generative Adversarial Networks (GANs) can be used to convert a PET image to a virtual SPECT image result, where the SPECT scan would be synthetically created. GANs are generative models where the goal is to learn the underlying training data distribution so as to generate new realistic data samples which are indistinguishable from the input dataset. FIG. 12 shows the different resolution of the PET compared to the SPECT scans. Both supervised and unsupervised technologies have been used for image to image translation. GANs can generate synthetic data with good generalization ability. GAN has two different networks Generator and Discriminator. The model is trained in an adversarial process where the Generator generates fake images, and the Discriminator learns to discriminate between the real and fake images. In this embodiment the input of the Generator is the images from a PET scan, and it learns to generate images in a SPECT scan. The discriminator examines these generated images based on the training images from PET scan and their corresponding images from the SPECT scan, and using the training data learns to distinguish between real and fake images. Based on the feedback from the discriminator, the generator learns to convert PET images into SPECT images more accurately.

In one embodiment, the conversion of the PET image to a virtual SPECT image can utilize the MLE that is trained on a dataset of PET and SPECT images across a large population. The input training vector set would include a vector for each patient representing the characteristics of the patient, as described above. The applied therapeutic radiopharmaceutical along with its dosage is also a variable in the training data set. Once the coefficients of the MLE are trained, a new PET scan can be input, along with a proposed dosage of a therapeutic radiopharmaceutical. The output of the MLE would be a predicted SPECT scan, the SPECT scan to be expected if the therapy is applied. The quality of the result can thereby be evaluated and an adjustment made to the dosage or even the selection of radiopharmaceutical in order to improve the expected outcome based on the MLE analysis. If the treatment is applied and an actual SPECT scan obtained, the predicted SPECT and actual SPECT may be compared in order to determine an error image or error value that can be used to calculate changes to the MLE coefficients, thereby improving the prediction iteratively. Over time, as the MLE operates across an ever larger and diverse data set, the actual SPECT may become unnecessary. Rather, a post treatment PET scan may be conducted to confirm the result. The training process can also take as input the ROI density in the outcome Pet Scan, and data representing the patient outcome.

In yet another embodiment, the post treatment result can be predicted based on the PET scan, the selected radiopharmaceutical to be administered and the dosage and timing of the dosages. In this embodiment, further post-treatment recurrence data and other patient histories can be extracted from EMR data in order to train the MLE to calculate the quality of the radiopharmaceutical treatment result by automatic analysis of the predicted outcome and the predicted likelihood of recurrence as an output. The output can be a number representing the quality of the result. For example, a quality value V can be the total predicted volume of tracked tumors post-treatment. The system can take the predicted treatment result output in the form of the tumor feature vectors at the end of the treatment. For each tumor, the volume of the tumor can be calculated and added to a running sum until all the tumor volume is calculated. If the result is more than a predetermined threshold, the dosage value and timing value of the administration of the radiopharmaceutical may be adjusted as an input into the MLE until the MLE output V is below the threshold. The value of the dosage and timing at that point is an prescription with an expected prediction of a successful treatment.

Operating Environment:

The system is typically comprised of a central server that is connected by a data network to a user's computer. The central server may be comprised of one or more computers connected to one or more mass storage devices. The precise architecture of the central server does not limit the claimed invention. Further, the user's computer may be a laptop or desktop type of personal computer. It can also be a cell phone, smart phone or other handheld device, including a tablet. The precise form factor of the user's computer does not limit the claimed invention. Examples of well-known computing systems, environments, and/or configurations that may be suitable for use with the invention include, but are not limited to, personal computers, server computers, handheld computers, laptop or mobile computer or communications devices such as cell phones, smart phones, and PDA's, multiprocessor systems, microprocessor-based systems, set top boxes, programmable consumer electronics, network PCs, minicomputers, mainframe computers, distributed computing environments that include any of the above systems or devices, and the like. Indeed, the terms "computer," "server," and the like may be used interchangeably herein, and may refer to any of the above devices and systems.

The user environment may be housed in the central server or operatively connected to it remotely using a network. In one embodiment, the user's computer is omitted, and instead an equivalent computing functionality is provided that works on a server. In this case, a user would log into the server from another computer over a network and access the system through a user environment, and thereby access the functionality that would in other embodiments, operate on the user's computer. Further, the user may receive from and transmit data to the central server by means of the Internet, whereby the user accesses an account using an Internet web-browser and browser displays an interactive web page operatively connected to the central server. The server transmits and receives data in response to data and commands transmitted from the browser in response to the customer's actuation of the browser user interface. Some steps of the invention may be performed on the user's computer and interim results transmitted to a server. These interim results may be processed at the server and final results passed back to the user.

The Internet is a computer network that permits customers operating a personal computer to interact with computer servers located remotely and to view content that is delivered from the servers to the personal computer as data files over the network. In one kind of protocol, the servers present webpages that are rendered on the customer's personal computer using a local program known as a browser. The browser receives one or more data files from the server that are displayed on the customer's personal computer screen. The browser seeks those data files from a specific address, which is represented by an alphanumeric string called a Universal Resource Locator (URL). However, the webpage may contain components that are downloaded from a variety of URL's or IP addresses. A website is a collection of related URL's, typically all sharing the same root address or under the control of some entity. In one embodiment different regions of the simulated space displayed by the browser have different URL's. That is, the webpage encoding the simulated space can be a unitary data structure, but different URL's reference different locations in the data structure. The user computer can operate a program that receives from a remote server a data file that is passed to a program that interprets the data in the data file and commands the display device to present particular text, images, video, audio and other objects. In some embodiments, the remote server delivers a data file that is comprised of computer code that the browser program interprets, for example, scripts. The program can detect the relative location of the cursor when the mouse button is actuated, and interpret a command to be executed based on location on the indicated relative location on the display when the button was pressed. The data file may be an HTML document, the program a web-browser program and the command a hyper-link that causes the browser to request a new HTML document from another remote data network address location. The HTML can also have references that result in other code modules being called up and executed, for example, Flash or other native code.

The invention may also be entirely executed on one or more servers. A server may be a computer comprised of a central processing unit with a mass storage device and a network connection. In addition a server can include multiple of such computers connected together with a data network or other data transfer connection, or, multiple computers on a network with network accessed storage, in a manner that provides such functionality as a group. Practitioners of ordinary skill will recognize that functions that are accomplished on one server may be partitioned and accomplished on multiple servers that are operatively connected by a computer network by means of appropriate inter process communication. In one embodiment, a user's computer can run an application that causes the user's computer to transmit a stream of one or more data packets across a data network to a second computer, referred to here as a server. The server, in turn, may be connected to one or more mass data storage devices where the database is stored. In addition, the access of the website can be by means of an Internet browser accessing a secure or public page or by means of a client program running on a local computer that is connected over a computer network to the server. A data message and data upload or download can be delivered over the Internet using typical protocols, including TCP/IP, HTTP, TCP, UDP, SMTP, RPC, FTP or other kinds of data communication protocols that permit processes running on two respective remote computers to exchange information by means of digital network communication. As a result a data message can be one or more data packets transmitted from or received by a computer containing a destination network address, a destination process or application identifier, and data values that can be parsed at the destination computer located at the destination network address by the destination application in order that the relevant data values are extracted and used by the destination application. The precise architecture of the central server does not limit the claimed invention. In addition, the data network may operate with several levels, such that the user's computer is connected through a fire wall to one server, which routes communications to another server that executes the disclosed methods.

The server can execute a program that receives the transmitted packet and interpret the transmitted data packets in order to extract database query information. The server can then execute the remaining steps of the invention by means of accessing the mass storage devices to derive the desired result of the query. Alternatively, the server can transmit the query information to another computer that is connected to the mass storage devices, and that computer can execute the invention to derive the desired result. The result can then be transmitted back to the user's computer by means of another stream of one or more data packets appropriately addressed to the user's computer. In addition, the user's computer may obtain data from the server that is considered a website, that is, a collection of data files that when retrieved by the user's computer and rendered by a program running on the user's computer, displays on the display screen of the user's computer text, images, video and in some cases outputs audio. The access of the website can be by means of a client program running on a local computer that is connected over a computer network accessing a secure or public page on the server using an Internet browser or by means of running a dedicated application that interacts with the server, sometimes referred to as an "app." The data messages may comprise a data file that may be an HTML document (or other hypertext formatted document file), commands sent between the remote computer and the server and a web-browser program or app running on the remote computer that interacts with the data received from the server. The command can be a hyper-link that causes the browser to request a new HTML document from another remote data network address location. The HTML can also have references that result in other code modules being called up and executed, for example, Flash, scripts or other code. The HTML file may also have code embedded in the file that is executed by the client program as an interpreter, in one embodiment, Javascript. As a result a data message can be a data packet transmitted from or received by a computer containing a destination network address, a destination process or application identifier, and data values or program code that can be parsed at the destination computer located at the destination network address by the destination application in order that the relevant data values or program code are extracted and used by the destination application.

The invention may also be practiced in distributed computing environments where tasks are performed by remote processing devices that are linked through a communications network. In a distributed computing environment, program modules may be located in both local and remote computer storage media including memory storage devices. Practitioners of ordinary skill will recognize that the invention may be executed on one or more computer processors that are linked using a data network, including, for example, the Internet. In another embodiment, different steps of the process can be executed by one or more computers and storage devices geographically separated by connected by a data network in a manner so that they operate together to execute the process steps. In one embodiment, a user's computer can run an application that causes the user's computer to transmit a stream of one or more data packets across a data network to a second computer, referred to here as a server. The server, in turn, may be connected to one or more mass data storage devices where the database is stored. The server can execute a program that receives the transmitted packet and interpret the transmitted data packets in order to extract database query information. The server can then execute the remaining steps of the invention by means of accessing the mass storage devices to derive the desired result of the query. Alternatively, the server can transmit the query information to another computer that is connected to the mass storage devices, and that computer can execute the invention to derive the desired result. The result can then be transmitted back to the user's computer by means of another stream of one or more data packets appropriately addressed to the user's computer. In one embodiment, a relational database may be housed in one or more operatively connected servers operatively connected to computer memory, for example, disk drives. In yet another embodiment, the initialization of the relational database may be prepared on the set of servers and the interaction with the user's computer occur at a different place in the overall process.

The method described herein can be executed on a computer system, generally comprised of a central processing unit (CPU) that is operatively connected to a memory device, data input and output circuitry (IO) and computer data network communication circuitry. Computer code executed by the CPU can take data received by the data communication circuitry and store it in the memory device. In addition, the CPU can take data from the I/O circuitry and store it in the memory device. Further, the CPU can take data from a memory device and output it through the IO circuitry or the data communication circuitry. The data stored in memory may be further recalled from the memory device, further processed or modified by the CPU in the manner described herein and restored in the same memory device or a different memory device operatively connected to the CPU including by means of the data network circuitry. In some embodiments, data stored in memory may be stored in the memory device, or an external mass data storage device like a disk drive. In yet other embodiments, the CPU may be running an operating system where storing a data set in memory is performed virtually, such that the data resides partially in a memory device and partially on the mass storage device. The CPU may perform logic comparisons of one or more of the data items stored in memory or in the cache memory of the CPU, or perform arithmetic operations on the data in order to make selections or determinations using such logical tests or arithmetic operations. The process flow may be altered as a result of such logical tests or arithmetic operations so as to select or determine the next step of a process. For example, the CPU may obtain two data values from memory and the logic in the CPU determine whether they are the same or not. Based on such Boolean logic result, the CPU then selects a first or a second location in memory as the location of the next step in the program execution. This type of program control flow may be used to program the CPU to determine data, or select a data from a set of data. The memory device can be any kind of data storage circuit or magnetic storage or optical device, including a hard disk, optical disk or solid state memory. The IO devices can include a display screen, loudspeakers, microphone and a movable mouse that indicate to the computer the relative location of a cursor position on the display and one or more buttons that can be actuated to indicate a command.

The computer can display on the display screen operatively connected to the I/O circuitry the appearance of a user interface. Various shapes, text and other graphical forms are displayed on the screen as a result of the computer generating data that causes the pixels comprising the display screen to take on various colors and shades or brightness. The user interface may also display a graphical object referred to in the art as a cursor. The object's location on the display indicates to the user a selection of another object on the screen. The cursor may be moved by the user by means of another device connected by I/O circuitry to the computer. This device detects certain physical motions of the user, for example, the position of the hand on a flat surface or the position of a finger on a flat surface. Such devices may be referred to in the art as a mouse or a track pad. In some embodiments, the display screen itself can act as a trackpad by sensing the presence and position of one or more fingers on the surface of the display screen. When the cursor is located over a graphical object that appears to be a button or switch, the user can actuate the button or switch by engaging a physical switch on the mouse or trackpad or computer device or tapping the trackpad or touch sensitive display. When the computer detects that the physical switch has been engaged (or that the tapping of the track pad or touch sensitive screen has occurred), it takes the apparent location of the cursor (or in the case of a touch sensitive screen, the detected position of the finger) on the screen and executes the process associated with that location. As an example, not intended to limit the breadth of the disclosed invention, a graphical object that appears to be a two dimensional box with the word "enter" within it may be displayed on the screen. If the computer detects that the switch has been engaged while the cursor location (or finger location for a touch sensitive screen) was within the boundaries of a graphical object, for example, the displayed box, the computer will execute the process associated with the "enter" command. In this way, graphical objects on the screen create a user interface that permits the user to control the processes operating on the computer.

In some instances, especially where the user computer is a mobile computing device used to access data through the network the network may be any type of cellular, IP-based or converged telecommunications network, including but not limited to Global System for Mobile Communications (GSM), Time Division Multiple Access (TDMA), Code Division Multiple Access (CDMA), Orthogonal Frequency Division Multiple Access (OFDM), General Packet Radio Service (GPRS), Enhanced Data GSM Environment (EDGE), Advanced Mobile Phone System (AMPS), Worldwide Interoperability for Microwave Access (WiMAX), Universal Mobile Telecommunications System (UMTS), Evolution-Data Optimized (EVDO), Long Term Evolution (LTE), Ultra Mobile Broadband (UMB), Voice over Internet Protocol (VoIP), Unlicensed Mobile Access (UMA), any form of 802.11.xx or Bluetooth.

Computer program logic implementing all or part of the functionality previously described herein may be embodied in various forms, including, but in no way limited to, a source code form, a computer executable form, and various intermediate forms (e.g., forms generated by an assembler, compiler, linker, or locator.) Source code may include a series of computer program instructions implemented in any of various programming languages (e.g., an object code, an assembly language, or a high-level language such as Javascript, C, C++, JAVA, or HTML or scripting languages that are executed by Internet web-browsers) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The invention may be described in the general context of computer-executable instructions, such as program modules, being executed by a computer. Generally, program modules include routines, programs, objects, binary components that, when executed by the CPU, perform particular tasks or implement particular abstract data types and when running, may generate in computer memory or store on disk, various data structures. A data structure may be represented in the disclosure as a manner of organizing data, but is implemented by storing data values in computer memory in an organized way. Data structures may be comprised of nodes, each of which may be comprised of one or more elements, encoded into computer memory locations into which is stored one or more corresponding data values that are related to an item being represented by the node in the data structure. The collection of nodes may be organized in various ways, including by having one node in the data structure being comprised of a memory location wherein is stored the memory address value or other reference, or pointer, to another node in the same data structure. By means of the pointers, the relationship by and among the nodes in the data structure may be organized in a variety of topologies or forms, including, without limitation, lists, linked lists, trees and more generally, graphs. The relationship between nodes may be denoted in the specification by a line or arrow from a designated item or node to another designated item or node. A data structure may be stored on a mass storage device in the form of data records comprising a database, or as a flat, parsable file. The processes may load the flat file, parse it, and as a result of parsing the file, construct the respective data structure in memory. In other embodiment, the data structure is one or more relational tables stored on the mass storage device and organized as a relational database.

The computer program and data may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed hard disk), an optical memory device (e.g., a CD-ROM or DVD), a PC card (e.g., PCMCIA card, SD Card), or other memory device, for example a USB key. The computer program and data may be fixed in any form in a signal that is transmittable to a computer using any of various communication technologies, including, but in no way limited to, analog technologies, digital technologies, optical technologies, wireless technologies, networking technologies, and internetworking technologies. The computer program and data may be distributed in any form as a removable storage medium with accompanying printed or electronic documentation (e.g., a disk in the form of shrink wrapped software product or a magnetic tape), preloaded with a computer system (e.g., on system ROM or fixed disk), or distributed from a server, website or electronic bulletin board or other communication system (e.g., the Internet or World Wide Web.) It is appreciated that any of the software components of the present invention may, if desired, be implemented in ROM (read-only memory) form. The software components may, generally, be implemented in hardware, if desired, using conventional techniques.

It should be noted that the flow diagrams are used herein to demonstrate various aspects of the invention, and should not be construed to limit the present invention to any particular logic flow or logic implementation. The described logic may be partitioned into different logic blocks (e.g., programs, modules, functions, or subroutines) without changing the overall results or otherwise departing from the true scope of the invention. Oftentimes, logic elements may be added, modified, omitted, performed in a different order, or implemented using different logic constructs (e.g., logic gates, looping primitives, conditional logic, and other logic constructs) without changing the overall results or otherwise departing from the true scope of the invention. Where the disclosure refers to matching or comparisons of numbers, values, or their calculation, these may be implemented by program logic by storing the data values in computer memory and the program logic fetching the stored data values in order to process them in the CPU in accordance with the specified logical process so as to execute the matching, comparison or calculation and storing the result back into computer memory or otherwise branching into another part of the program logic in dependence on such logical process result. The locations of the stored data or values may be organized in the form of a data structure.

The described embodiments of the invention are intended to be exemplary and numerous variations and modifications will be apparent to those skilled in the art. All such variations and modifications are intended to be within the scope of the present invention as defined in the appended claims. Although the present invention has been described and illustrated in detail, it is to be clearly understood that the same is by way of illustration and example only, and is not to be taken by way of limitation. It is appreciated that various features of the invention which are, for clarity, described in the context of separate embodiments may also be provided in combination in a single embodiment. Conversely, various features of the invention which are, for brevity, described in the context of a single embodiment may also be provided separately or in any suitable combination. It is appreciated that the particular embodiment described in the Appendices is intended only to provide an extremely detailed disclosure of the present invention and is not intended to be limiting.

The foregoing description discloses only exemplary embodiments of the invention. Modifications of the above disclosed apparatus and methods which fall within the scope of the invention will be readily apparent to those of ordinary skill in the art. Accordingly, while the present invention has been disclosed in connection with exemplary embodiments thereof, it should be understood that other embodiments may fall within the spirit and scope of the invention as defined by the following claims.

What is claimed:

1. A method performed by a computer system comprised of a first machine learning engine for calculating a predicted therapeutic result image for a patient undergoing a radiopharmaceutical treatment comprising:
   receiving at the computer system a first diagnostic scan data derived from a diagnostic scan of a patient;
   receiving at the computer system an identity data of the diagnostic radiopharmaceutical;
   receiving at the computer system an at least one data parameters that each represent at least one corresponding medical characteristics of the patient;
   receiving at the computer system an identity data of a therapeutic radiopharmaceutical and a corresponding data representing an at least one dosage amount of the radiopharmaceutical and a data representing a corresponding at least one timing value corresponding to the at least one dosage amount of the therapeutic radiopharmaceutical;
   inputting into the first machine learning engine the received first diagnostic scan data, the received identity data of the diagnostic radiopharmaceutical, the received at least one data parameters representing characteristics of the patient, the received identity data of the therapeutic radiopharmaceutical and the data representing the at least one dosage amount of the radiopharmaceutical and the corresponding at least one timing value of the dosage of the therapeutic radiopharmaceutical; and
   using the machine learning engine to automatically generate a predicted therapeutic image result scan data indicative of an expected effectiveness of the therapeutic radiopharmaceutical in the patient using the received first diagnostic scan data, the received at least one data parameters representing medical characteristics of the patient, the identity data of the therapeutic radiopharmaceutical and the data representing at least one dosage amount of the therapeutic radiopharmaceutical and the corresponding at least one timing value of the dosage of the therapeutic radiopharmaceutical.

2. The method of claim 1 further comprising:
   receiving at the computer system a prediction time value data;
   inputting into the first machine learning engine data comprised of the received prediction time value data.

3. The method of claim 1 further comprising:
   generating the diagnostic scan data by receiving data representing detected radioactive emissions of the radiopharmaceutical administered to the patient.

4. The method of claim 1 where the diagnostic scan data is a positron emission tomography (PET) scan image.

5. The method of claim 1 where the predicted therapeutic result scan image is a can image predicting the distribution of the therapeutic radiopharmaceutical's radioactivity in the patient.

6. The method of claim 1 where the predicted therapeutic result scan image is a scan image predicting the distribution of the tumor tissue in the patient as a result of the therapeutic radiopharmaceutical.

7. The method of claim 1 where the predicted therapeutic result scan image data represents an absorbed dose map of the therapeutic radiopharmaceutical.

8. The method of claim 1 further comprising:
   receiving a data representing a targeted region of interest;
   receiving a data representing a maximum permissible radiodosage threshold; and
   inputting the targeted region of interest data and maximum permissible radiodosage threshold data into the first machine learning engine.

9. The method of claim 1 further comprising:
   receiving a prior therapeutic scan data corresponding to the patient for the same treatment; and
   inputting the prior therapeutic scan data corresponding to the patient into the first machine learning engine to calculate a new predicted therapeutic image.

10. The method of claim 1 where the first machine learning engine is a neural network.

11. The method of claim 10 where the machine learning engine is at least one of: a convolutional residual network, a recurrent neural Network or a contextual LSTM.

12. The method of claim 1 where the predicted therapeutic result scan image data represents a prediction of a diagnostic or therapeutic scan image.

13. The method of claim 12 where the predicted therapeutic result scan image data represents a prediction of a positron emission tomography (PET) scan image.

14. The method of claim 12 where the predicted therapeutic result scan image is a magnetic resonance imaging (MRI) scan.

15. The method of claim 1 further comprising:
using the first machine learning engine to calculate a therapeutic dosage data for the therapeutic radiopharmaceutical.

16. The method of claim 15 further comprising:
using the first machine learning engine to calculate a maximum permissible radiodosage threshold for the radiopharmaceutical.

17. The method of claim 1 further comprising:
generating a dosimetry report comprising an image comprised of a three-dimensional (3D) image comprised of voxels of a predetermined size where for each voxel there is a value representing standard units of radiation activity.

18. The method of claim 17 where the generating a dosimetry report step is comprised of:
receiving one of a post-therapeutic positron emission tomography (PET) scan or a post-therapeutic computed axial tomography (CAT) scan or a post-therapeutic magnetic resonance imaging (MRI) scan;
inputting the post-therapeutic scan data into a dosimetry machine learning engine; and
using the dosimetry machine learning engine to generate a synthetic single-photon emission computerized tomography (SPECT) scan from the post-therapeutic scan data.

19. The method of claim 1 further comprising:
generating at least one predicted therapeutic image data using a corresponding at least one type of therapeutic radiopharmaceutical.

20. The method of claim 19 further comprising:
inputting the generated at least one predicted therapeutic image data into the first machine learning engine and
using the first machine learning engine to determine which of the at least one radiopharmaceutical types produce the greatest predicted change between the diagnostic image data input corresponding to the patient and the predicted therapeutic image data output corresponding to the patient.

21. The method of claim 1 further comprising:
inputting an at least one diagnostic scan data corresponding to the patient into a second machine learning engine;
using the second machine learning engine to generate a corresponding at least one data output representing an organ segmentation data output for the patient; and
inputting the organ segmentation data into the first machine learning engine.

22. The method of claim 21 where one of the at least one diagnostic scan data input into the second machine learning engine is a computed axial tomography (CAT) scan data.

23. The method of claim 21 where one of the at least one diagnostic scan input into the second machine learning engine is a magnetic resonance imaging (MRI) scan data.

24. The method of claim 21 further comprising:
inputting one of the diagnostic scan or the therapeutic result scan corresponding to the patient into a third machine learning engine;
using the third machine learning engine to generate a tumor tracking and analysis data; and
inputting the tumor tracking and analysis data into the first machine learning engine.

25. The method of claim 24 where the generating tumor tracking and analysis data is comprised of identifying tumor locations;
determining tumor geometry;
and generating a data structure representing the change in the tumor geometry over time.

26. A method of configuring a machine learning engine for generating a predicted therapeutic result image data corresponding to a patient comprising:
receiving at the computer system at least one diagnostic scan data derived from a corresponding diagnostic scan of the patient;
receiving at the computer system an at least one identity data of a diagnostic radiopharmaceutical corresponding to the at least one diagnostic scan data;
receiving at the computer system an at least one data parameters that encode physical characteristics of the patient corresponding to the at least one diagnostic scan;
receiving at the computer system an at least one data representing a corresponding at least one dosage amount of the corresponding therapeutic radiopharmaceutical and a corresponding at least one timing value corresponding to the dosage amount;
receiving at the computer at least one therapeutic scan data corresponding to the patient and a timing data corresponding to the therapeutic scan data;
inputting into the machine learning engine the received at least one diagnostic scan data, the received at least one data parameters representing characteristics of the at least one patient, the at least one identity data of the therapeutic radiopharmaceutical and the at least one data representing the dosage amount and the corresponding at least one timing value corresponding to the dosage amount and the at least one timing data corresponding to the therapeutic scan data; and
using the machine learning engine to automatically generate a predicted therapeutic image data using the data comprising the received at least one diagnostic scan data,
the received at least one data parameters representing characteristics of the at least one patient, the at least one identity data of the therapeutic radiopharmaceutical and the at least one data representing the dosage amount and the corresponding at least one timing value corresponding to the dosage amount and the at least one timing data corresponding to the therapeutic scan data;
calculating an at least one error data using the predicted therapeutic image data and the at least one therapeutic scan data;
changing an at least one stored coefficient data comprising the machine learning engine in dependence on the at least one calculated error data.

27. The method of claim 26 further comprising:
receiving data representing tumor recurrence data for at least one patient;

inputting the tumor recurrence data into the first machine learning engine.

28. The method of claim 26 further comprising:
inputting into the machine learning engine annotated human training data that is comprised of data that identifies at least one organ.

* * * * *